US 10,682,119 B2

United States Patent
Sudol

(10) Patent No.: US 10,682,119 B2
(45) Date of Patent: Jun. 16, 2020

(54) SHAPE SENSING FOR FLEXIBLE ULTRASOUND TRANSDUCERS

(71) Applicant: KONINKLIJKE PHILIPS N.V., Eindhoven (NL)

(72) Inventor: Wojtek Sudol, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 540 days.

(21) Appl. No.: 15/520,473

(22) PCT Filed: Oct. 9, 2015

(86) PCT No.: PCT/IB2015/057718
§ 371 (c)(1),
(2) Date: Apr. 20, 2017

(87) PCT Pub. No.: WO2016/063163
PCT Pub. Date: Apr. 28, 2016

(65) Prior Publication Data
US 2017/0311924 A1 Nov. 2, 2017

Related U.S. Application Data

(60) Provisional application No. 62/067,583, filed on Oct. 23, 2014.

(51) Int. Cl.
*A61B 8/00* (2006.01)
*A61B 8/12* (2006.01)

(52) U.S. Cl.
CPC ............ *A61B 8/4254* (2013.01); *A61B 8/429* (2013.01); *A61B 8/4494* (2013.01); *A61B 8/12* (2013.01); *A61B 8/4488* (2013.01)

(58) Field of Classification Search
CPC ..... A61B 8/4494; A61B 8/429; A61B 8/4254; A61B 8/12; A61B 8/4488
See application file for complete search history.

(56) References Cited

U.S. PATENT DOCUMENTS

| | | | | |
|---|---|---|---|---|
| 5,500,635 | A | * 3/1996 | Mott | A43B 1/0072 310/311 |
| 5,913,825 | A | * 6/1999 | Watanabe | A61B 8/4281 600/459 |
| 6,443,896 | B1 | 9/2002 | Detmer | |

(Continued)

FOREIGN PATENT DOCUMENTS

| | | | | |
|---|---|---|---|---|
| JP | 2011183057 | A * | 9/2011 | ........... A61B 5/0091 |
| WO | 2014167511 | A1 | 10/2014 | |

OTHER PUBLICATIONS

Christopher J.L. Lane: "The inspection of curved components using flexible ultrasonic arrays and shape sensing fibres",Case Studies in Nondestructive Testing and Evaluation,vol. 1, Apr. 1, 2014 (Apr 1, 2014), p. 13-18.

*Primary Examiner* — Bo Joseph Peng

(57) ABSTRACT

A transducer device includes a transducer array (300) configured on a substrate (312). The substrate is configured to flex in accordance with a surface. The transducer array includes elements for transmitting and/or receiving acoustic energy. A shape sensing optical fiber (314) is disposed within the array and configured to shape sense a position of the elements in the array. Stiffeners (308) are connected to the array and configured to flex in accordance with the surface and provide a limit to an amount of flexure.

13 Claims, 6 Drawing Sheets

(56) References Cited

U.S. PATENT DOCUMENTS

| | | | |
|---|---|---|---|
| 6,517,484 B1* | 2/2003 | Wilk | A61B 8/00 600/437 |
| 6,530,885 B1 | 3/2003 | Entrekin et al. | |
| 7,520,175 B2 | 4/2009 | Ko et al. | |
| 8,120,759 B2 | 2/2012 | Olesen | |
| 2005/0004458 A1* | 1/2005 | Kanayama | A61B 5/0091 600/437 |
| 2007/0078345 A1* | 4/2007 | Mo | A61B 8/12 600/459 |
| 2007/0167800 A1* | 7/2007 | Casula | G10K 11/346 600/459 |
| 2009/0024034 A1 | 1/2009 | Moreau-Gobard | |
| 2010/0191119 A1* | 7/2010 | Muthya | A61B 8/02 600/453 |
| 2010/0280416 A1* | 11/2010 | Hyde | A61B 5/103 600/587 |
| 2012/0277639 A1* | 11/2012 | Pollock | B06B 1/0629 601/2 |
| 2012/0316419 A1* | 12/2012 | Chevalier | A61B 5/02007 600/381 |
| 2013/0177281 A1* | 7/2013 | Kosenko | G02B 6/4214 385/89 |
| 2013/0211261 A1* | 8/2013 | Wang | A61B 5/055 600/476 |

* cited by examiner

SHAPE SENSING FOR FLEXIBLE ULTRASOUND TRANSDUCERS

This application is the U.S. National Phase application under 35 U.S.C. § 371 of International Application No. PCT/IB2015/057718, filed on Oct. 9, 2015, which claims the benefit of Provisional Application Ser. No. 62/067,583, filed Oct. 23, 2014. These applications are hereby incorporated by reference herein.

BACKGROUND

Technical Field

This disclosure relates to imaging devices and more particularly to an imaging transducer having a shape sensing optical fiber for time delay compensation.

Description of the Related Art

In ultrasound imaging applications, to know how to beamform transmit and receive signals from a transducer array, it is often relevant to know exact relative positions of the different transducer elements. If a position of the element in space is not known, then imaging information gathered from the patient is not useful. In many imaging scenarios, an imaging probe with fixed sensors is difficult to use on the human body, and imaging suffers when transducers are not in direct contact with the body and ultrasound waves are not properly coupled to the body.

Due to the topography of the human body, local positions of transducers may not be known. To achieve acoustic beam focus and steering, a precise geometrical position of all elements is needed.

SUMMARY

In accordance with the present principles, a transducer device includes a transducer array configured on a substrate. The substrate is configured to flex in accordance with a surface, and the transducer array includes a plurality of elements for transmitting and/or receiving acoustic energy. At least one shape sensing optical fiber is disposed within the array and configured to shape sense a position of at least one element in the array. A plurality of stiffeners is connected to the array and configured to flex in accordance with the surface and provide a limit to an amount of flexure.

A transducer system includes a transducer device having a transducer array configured on a substrate. The substrate is configured to flex in accordance with a surface, and the transducer array includes a plurality of elements for transmitting and/or receiving acoustic energy. At least one shape sensing optical fiber is disposed within the array and is configured to shape sense a position of at least one element in the array. A plurality of stiffeners is connected to the array, is configured to flex in accordance with the surface and provides a limit to an amount of flexure. A shape sensing module is configured to receive optical signals from the at least one shape sensing optical fiber and interpret the optical signals to be used in determining time delays based on positions of the elements due to flexure.

A method for flexible transducing includes providing a transducer device having a transducer array configured on a substrate, the substrate being configured to flex in accordance with a surface, the transducer array including a plurality of elements for transmitting and/or receiving acoustic energy, at least one shape sensing optical fiber disposed within the array and configured to shape sense a position of at least one element in the array and a plurality of stiffeners connected to the array, configured to flex in accordance with the surface and provide a limit to an amount of flexure; positioning the transducer device at the surface for imaging such that the array flexes in accordance with the surface; determining positional changes in the array on the surface using the at least one shape sensing optical fiber disposed within the array and compensating for time delays due to the positional changes to improve ultrasonic beam focus.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
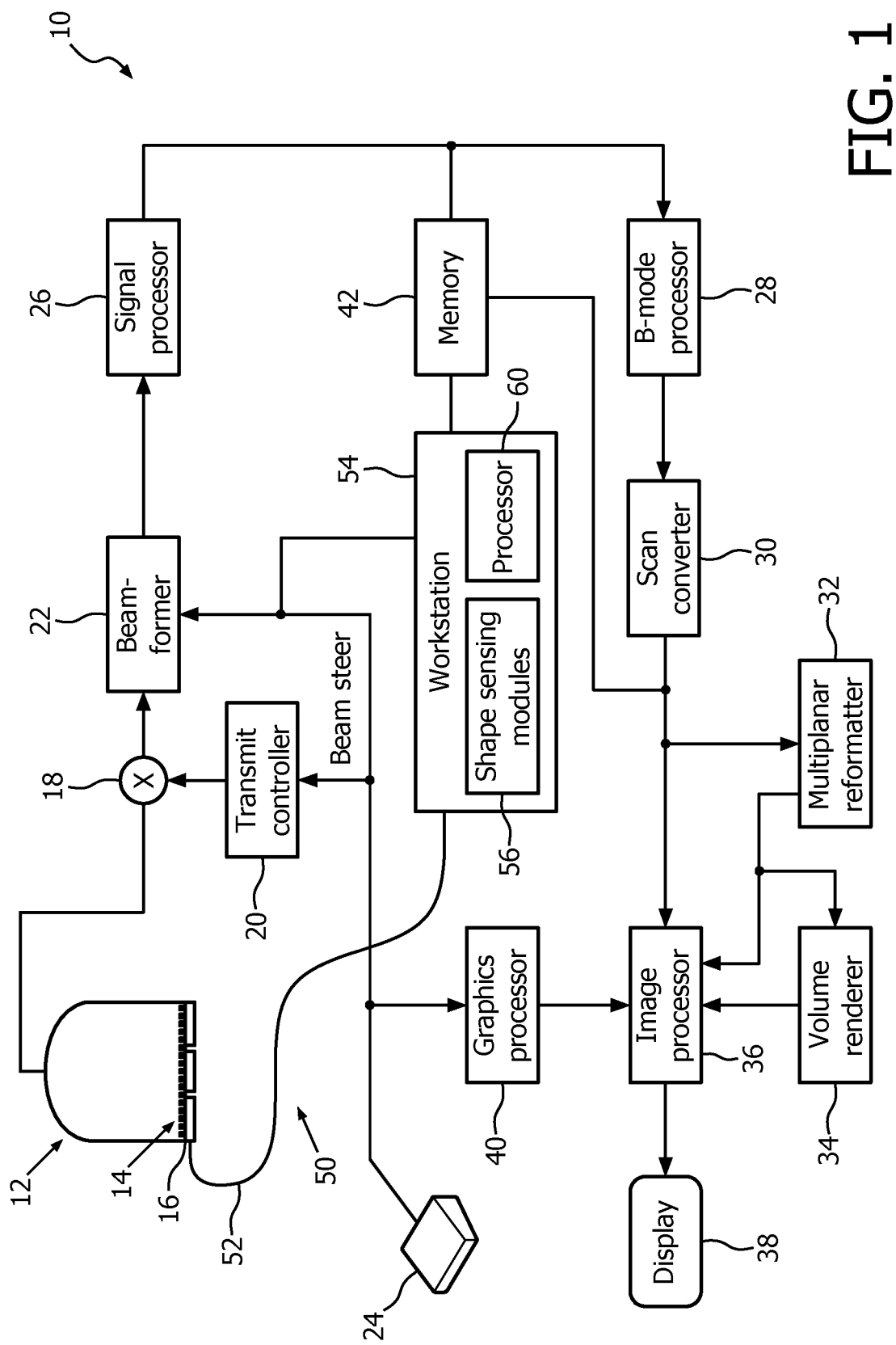
FIG. 1 is a block/flow diagram showing an ultrasonic imaging system having a shape sensing system in a transducer array in accordance with one embodiment.

In accordance with the present principles, a flexible ultrasound transducer array is provided, and individual transducer elements are positionally tracked using one or more optical shape sensing fibers. The optical shape sensing fibers define relative positions of the elements with respect to a reference position. In this way, a position of all transducer elements can be known in real-time. In one embodiment, the transducer array may include rigid or semi-rigid tiles or stiffeners. The stiffeners may be made of a plurality of different useful materials. The stiffeners may be employed to limit the motion (e.g., limit deformation to only one plane) of the individual transducers relative to the others and be sized to enable conformity with the human body.

Optical shape sensing (OSS) fibers may be associated with the stiffeners in a variety of ways, e.g., the OSS fibers may be threaded through, on and between the stiffeners to determine relative positions between the stiffeners. In addition, since the stiffeners can be linked to constrain motion, the number of OSS fibers can be kept to a minimum number.

In addition, by employing a stiffener structure, a manufacturing surface is provided (e.g., silicon or other material) to build or mount integrated circuits, e.g., application specific integrated circuits (ASICs), that can couple to elements of the array. In particularly useful embodiments, the stiffeners can be coupled or connected together in a plurality of different ways to achieve different degrees of freedom. For example, the stiffeners may be arranged on fabric, linked centrally, adhered to a polymer, etc. Depending on the arrangement of stiffeners, a configuration for the OSS fibers can be employed to allow for the selected degrees of freedom.

The OSS fiber embedded in the array continuously updates positions of all elements allowing timing correction compensation. The position of each element is therefore known at transmit and receive times.

It should be understood that aspects of the present invention will be described in terms of medical imaging; however, the teachings of the present invention are much broader and are applicable to any imaging system that benefits from the use of shape sensing optical fibers. The procedures described herein may be conducted for imaging in all areas of the body such as the lungs, gastro-intestinal tract, excretory organs, blood vessels, etc. and/or in mechanical systems for crack detection, material or structure integrality testing, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, certain aspects of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, an ultrasound imaging system 10 constructed in accordance with the present principles is shown in block diagram form. The ultrasound system 10 includes a flexible transducer device or probe 12 having a transducer array 14 for transmitting ultrasonic waves and receiving echo information. The transducer array may be configured as, e.g., linear arrays or phased arrays, and can include piezoelectric elements or capacitive micromachined ultrasonic transducers (CMUT) elements. The transducer array 14, for example, can include a two dimensional array (as shown) of transducer elements capable of scanning in both elevation and azimuth dimensions for 2D and/or 3D imaging. The flexible transducer device can be in various forms, e.g., as a flexible patch-like structure that can be readily laid on a patient for imaging, or the flexible transducer device can be incorporated into a traditional probe-type structure.

In accordance with the present principles, the transducer array 14 includes an optical shape sensing system 50 disposed therein. The shape sensing system 50 on or in transducer array 14 includes one or more optical fibers 52 which are coupled to the array 14 in a set pattern or patterns. The optical fibers 52 may connect to a workstation 54, which includes one or more shape sensing modules 56 for interpreting optical feedback from the optical fibers 52 to determine positions and orientations of transducer elements in the array 14.

Shape sensing system 50 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measured parameter (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. In high resolution ultrasound applications, the positional accuracy of the elements should be about 0.1 mm or better. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined. As an alternative to fiberoptic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

The transducer array 14 is coupled to a microbeamformer 16 in the probe 12, which controls transmission and reception of signals by the transducer elements in the array. In this example, the microbeamformer 16 is integrated with the flexible transducer device 12 and is coupled to a transmit/receive (T/R) switch 18, which switches between transmission and reception and protects a main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by a transmit controller 20 coupled to the T/R switch 18 and the beamformer 22, which may receive input from the user's operation of a user interface or control panel 24.

One function controlled by the transmit controller 20 is the direction in which beams are steered. Beams may be steered straight ahead from (orthogonal to) the transducer array, or at different angles for a wider field of view. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B mode processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer), which is incorporated herein by reference in its entirety. A volume renderer 34 converts the echo signals of a 3D data set into a projected 3D image as viewed from a given reference point, e.g., as described in U.S. Pat. No. 6,530,885 (Entrekin et al.), which is incorporated herein by reference in its entirety. The 2D or 3D images are coupled from the scan converter 30, multiplanar reformatter 32, and volume renderer 34 to an image processor 36 for further enhancement, buffering and temporary storage for display on an image display 38. A graphics processor 40 can generate graphic overlays for display with the ultrasound images. These graphic overlays or parameter blocks can contain, e.g., standard identifying information such as patient name, date and time of the image, imaging parameters, frame indices and the like. For these purposes, the graphics processor 40 receives input from the user interface 24, such as a typed patient name. The user interface 24 can also be coupled to the multiplanar reformatter 32 for selection and control of a display of multiple multiplanar reformatted (MPR) images.

In accordance with the present principles, ultrasound data is acquired and stored in memory 42 along with position and orientation data obtained from the shape sensing system 50. The memory 42 is depicted as being centrally placed; however, the memory 42 may store data and interact at any position in the signal path.

The workstation or console 54 may include one or more processors 60 and include its own memory (modules 56) or connect to memory 42 for storing programs and applications. Modules 56 are configured to interpret optical feedback signals from a shape sensing device or system 50. Optical sensing module 56 is configured to use the optical signal feedback to reconstruct deformations, deflections and other changes associated with the transducer array 14. The shape sensing optical fiber(s) 52 continuously updates the system 10 with the location of all the transducer elements in transducer array 14. The modules 56 respond with corrections to the timing of firing elements based on position to achieve a desired focus and beam steering. These corrections are employed by the graphics processor 40 and/or the image processor 36 to make image adjustments in accordance with time compensated image signals. In addition, the corrections may be employed as feedback for correcting a beam steering signal (Beam Steer) in accordance with the positions of the elements in the array 14.

Workstation 54 may connect to the display 38 for viewing internal images of a subject (patient) or volume. Display 38 may also permit a user to interact with the workstation 54 and its components and functions, or any other element within the system 10. This is further facilitated by the interface 24, which may include a keyboard, mouse, a joystick, a haptic device, or any other peripheral or control to permit user feedback from and interaction with the workstation 54.

Figure 2:
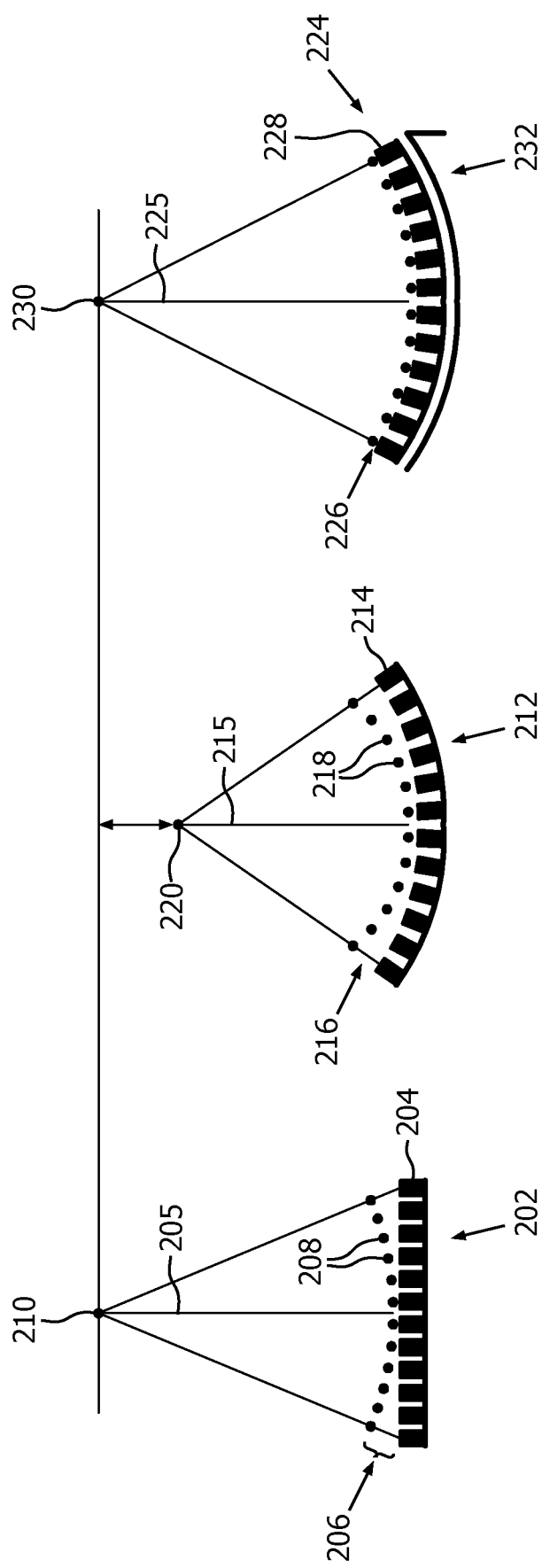
FIG. 2 is a diagram showing time delay and time compensation in different transducer array configurations in accordance with the present principles.

Referring to FIG. 2, an illustrative diagram demonstrates time compensation for transmitting and receiving ultrasound energy provided in accordance with embodiments of the present principles. A flat array 202 includes a plurality of transducer elements 204. The transducer elements 204 are distributed over a distance (e.g., displaced from a centerline 205). Energy from the transducer elements 204 is focused to a focal point 210. Due to the distribution, the distance from the focal point 210 to each element is different. This results in a time difference 208, 218, 228 that needs to be accounted for during beam forming. A time delay 206 is greater the further the transducer elements 204 are from the centerline 205. In the flat array 202, compensation is simple if the array 202 is not flexed.

If the array is flexed or undergoes bending, as depicted in array 212, the time delay adjustment is more difficult to determine. The array 212 includes a plurality of transducer elements 214. The transducer elements 214 are distributed over a distance (e.g., displaced from a centerline 215), but now undergo additional bending during operation. Energy from the transducer elements 214 is focused to a focal point 220, which is now shorter due to the additional mechanical focus changes due to bending. As a result of the distribution, the distance from the focal point 220 to each element 214 is different and is less predictable than for the flat array 202. A time delay 216 is much more difficult to evaluate and can result in a higher probability of out-of-focus images.

In accordance with the present principles, a shape sensing optical fiber or fibers 232 are provided to determine the amount of bending or flexure in an array 222 of transducer elements 224. The shape sensing optical fiber or fibers 232 are employed to determine the position and orientation of the transducer elements 224. Knowing the amount of bending, a more accurate estimate can be made for time delay compensation. The time delay adjustment may be computed directly from the output of the shape sensing optical fiber information. The transducer elements 224 are distributed over a distance (e.g., displaced from a centerline 225), but despite undergoing additional bending during operation can be time delay compensated. Energy from the transducer elements 224 is focused to a focal point 230, which is now the same as the flat array 202 as delay compensation includes delays caused by flexing or bending the array 222. A time delay 226 is easily determined and compensated for resulting in a higher probability of in-focus images.

Figure 3:
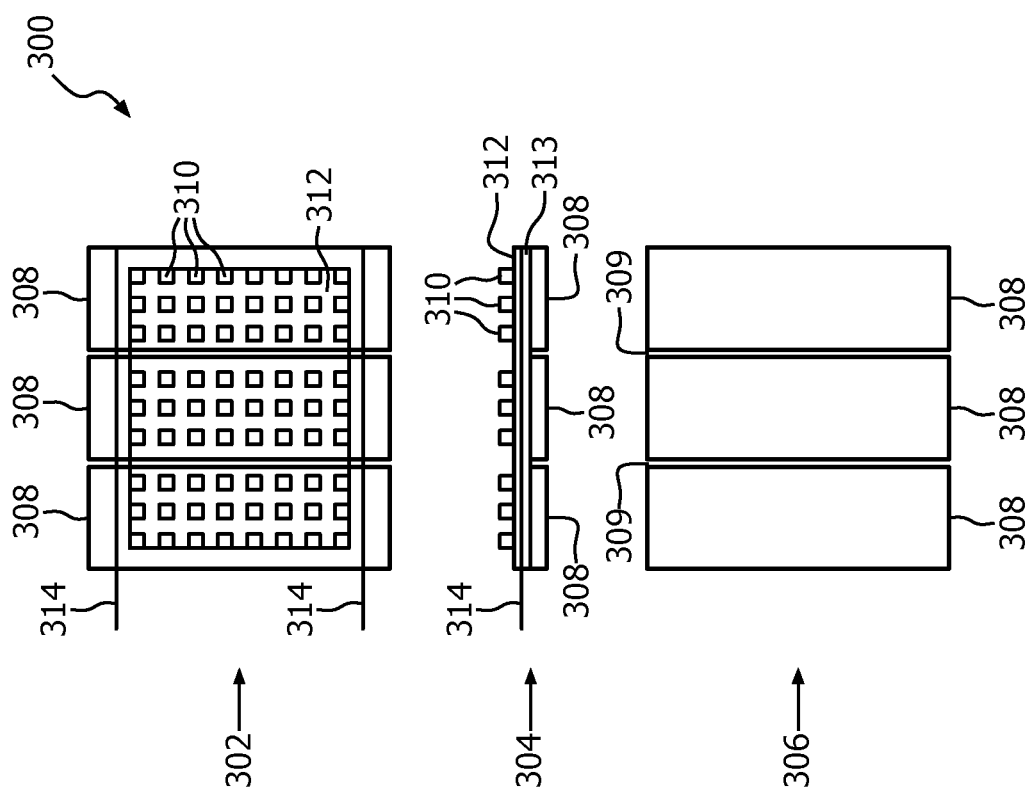
FIG. 3 shows top, side and bottom views of a flexible transducer device in accordance with one illustrative embodiment.

Referring to FIG. 3, a top view 302, side view 304 and bottom view 306 are shown of a matrix transducer array 300 in accordance with the present principles. Transducers 310 in the array 300 are formed on a substrate 312. The transducers 310 may include a piezoelectric material (e.g., PZT or the like). The substrate 312 may provide mechanical support and circuitry for activating the transducers 310. The substrate 312 may include an application specific integrated circuit (ASIC). The integrated circuit may include circuitry such as microbeamformer circuitry for use in an imaging probe. The substrate 312 may have a thickness of between about 10 to about 50 microns and permit flexure/bending to accommodate a subject (e.g., patient anatomy). The substrate 312 may include a mounting layer 313 configured to embed at least one shape sensing optical fiber 314. The mounting layer 313 may include an adhesive, epoxy, urethane or other material that can flexibly hold the shape sensing optical fiber 314.

The substrate 312 (or the mounting layer 313) is coupled to a plurality of tiles or stiffeners 308. The stiffeners 308 are depicted having a rectilinear shape; however, it should be understood that the stiffeners 308 may include any shape and may vary in size and pitch. In the embodiment depicted in FIG. 3, the stiffeners 308 extend along the array 300 and limit the flexure of the array 300, by permit bending along seams 309. The shape sensing optical fiber or fibers 314 may be mounted perpendicularly to the seams 309 and measure the bending orientation of each stiffener 308.

The stiffeners 308 may have a thickness of e.g., between about 1000 to about 3000 microns. In the configuration shown in FIG. 3, the stiffeners 308 permit array flexing in one plane only. If the substrate 312 includes silicon, silicon is not able to flex in two directions simultaneously. The stiffeners 308 also serve as a flexing limiter. The seams 309 (gaps) between the stiffeners 308 limit flexing the array 300 in the convex direction and other features can be added to limit the flexing in concave direction (e.g., wires anchored at both ends or other mechanical bend limiters (e.g., interlocking links, etc.)).

The stiffeners 308 may be formed from any useful material, but preferably include a high stiffness and low coefficient of thermal expansion and are compatible mechanically and electrically with the selected substrate 312 and other surrounding materials.

In useful embodiments, the amount of flexure can be tailored for a specific clinical application. For example, stiffeners 308 may be used to make the flexible transducer device more rigid for abdominal imaging as compared to breast imaging. In some aspects, the stiffeners can be connected together in different ways to make the flexure more or less rigid. When tailoring the flexibility, one transducer device can be employed for different applications that may need different levels of flexibility. For example, imaging of different sizes of anatomy (e.g., breasts) may need less or more flexibility in the transducer device. A user can simply lock together different stiffeners to modify the amount of flexure available for a specific application.

In other embodiments, different configurations may be employed to address specific concerns. For example, different type of layers, different sized layers, different stiffener configurations, different numbers and mountings of shape sensing fibers, etc. may be employed.

Figure 4:
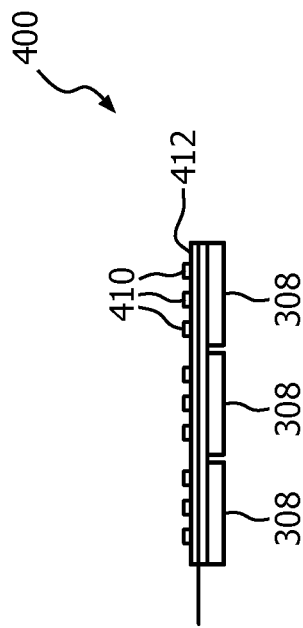
FIG. 4 shows a top view of a flexible transducer device having a reduced thickness to increase flexibility in accordance with another illustrative embodiment.

Referring to FIG. 4, in one embodiment, greater flexibility of the array may be needed. In one example, capacitive micromachined ultrasonic transducers (CMUT) 410 may be employed to form an array 400. Transducers 410 are much thinner than piezoelectric materials and, as such, a more flexible array 400 is achieved. The substrate 412 may also be made thinner, as well as other components of the array 400. The substrate 412 may include circuitry (integrated circuit (s)) to provide microbeamformer circuitry or the like for use in an imaging probe.

Figure 5:
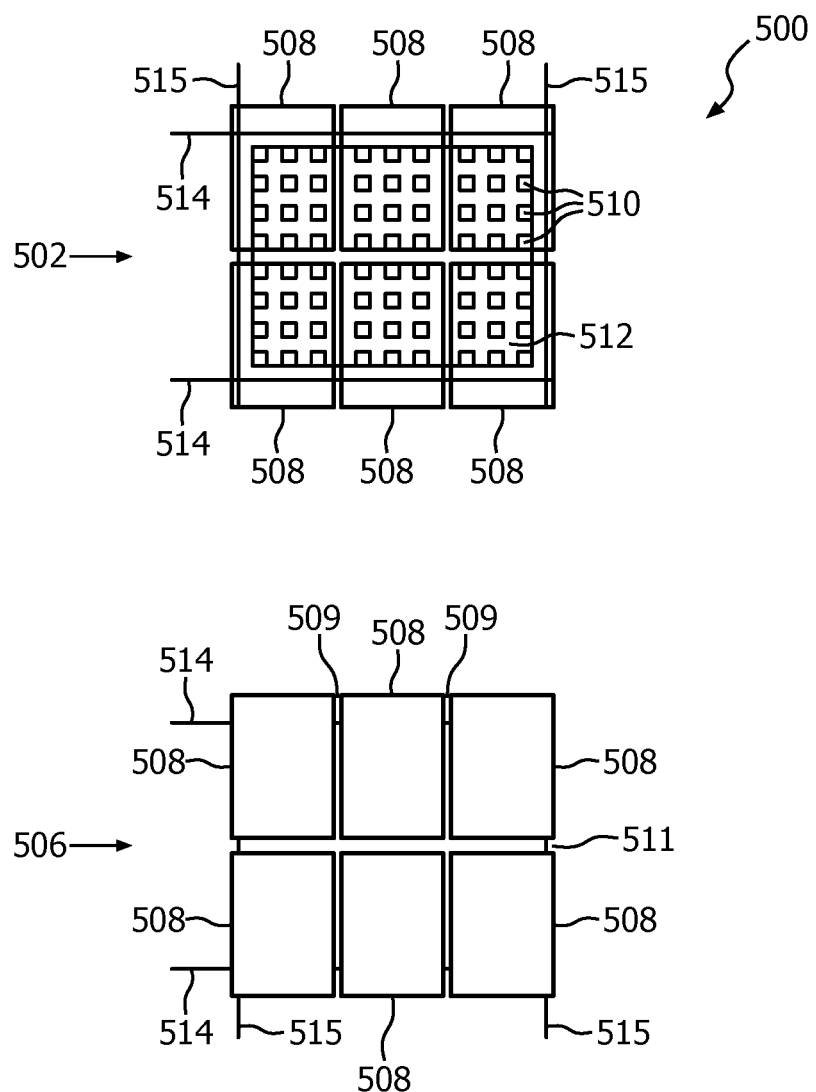
FIG. 5 shows top and bottom views of a flexible transducer device having tiles or stiffeners arranged in two dimensions in accordance with another illustrative embodiment.

Referring to FIG. 5, a top view 502 and bottom view 506 are shown of a matrix transducer array 500 in accordance with another embodiment. Transducers 510 in the array 500 are formed on a substrate 512. The transducers 510 may include a piezoelectric material (e.g., PZT or the like) or may be CMUTs. The substrate 512 may provide mechanical support and circuitry for activating the transducers 510. The substrate 512 may include an application specific integrated circuit (ASIC) formed on a flexible substrate, e.g., plastic, fabric, ceramic, etc. The integrated circuit may include circuitry such as microbeamformer circuitry for use in an imaging probe. The substrate 512 may have a thickness that permits flexure/bending in at least two directions. The substrate 512 may be configured to embed shape sensing optical fibers 514 and 515. The substrate 512 may include an adhesive, epoxy, urethane or other material that can flexibly pot or hold the shape sensing optical fibers 514 and 515. The substrate 512 may also include semiconductor or other materials.

The substrate 512 is coupled to a plurality of tiles or stiffeners 508. The stiffeners 508 are depicted having a rectilinear shape; however, it should be understood that the stiffeners 508 may include any shape and may vary in size and pitch. In the embodiment depicted in FIG. 5, the stiffeners 508 extend along the array 500 in two dimensions to support bending in two planes and limit the flexure of the array 500, by permitting bending along seams or gaps 509 and 511. The shape sensing optical fiber or fibers 514 and 515 may be mounted perpendicularly to the seams 509 and 511 respectively and measure the bending orientation of each stiffener 508.

The stiffeners 508 may have a thickness of e.g., between about 1000 to about 3000 microns. In the configuration shown in FIG. 5, the stiffeners 508 permit array flexing in two planes. The stiffeners 508 serve as a flexing limiter. The seams or gaps 509, 511 between the stiffeners 508 can limit flexing. The stiffeners 508 may be formed from any useful material, but preferably include a high stiffness and low coefficient of thermal expansion and are compatible mechanically and electrically with the selected substrate 512 and other surrounding materials.

Figure 6:
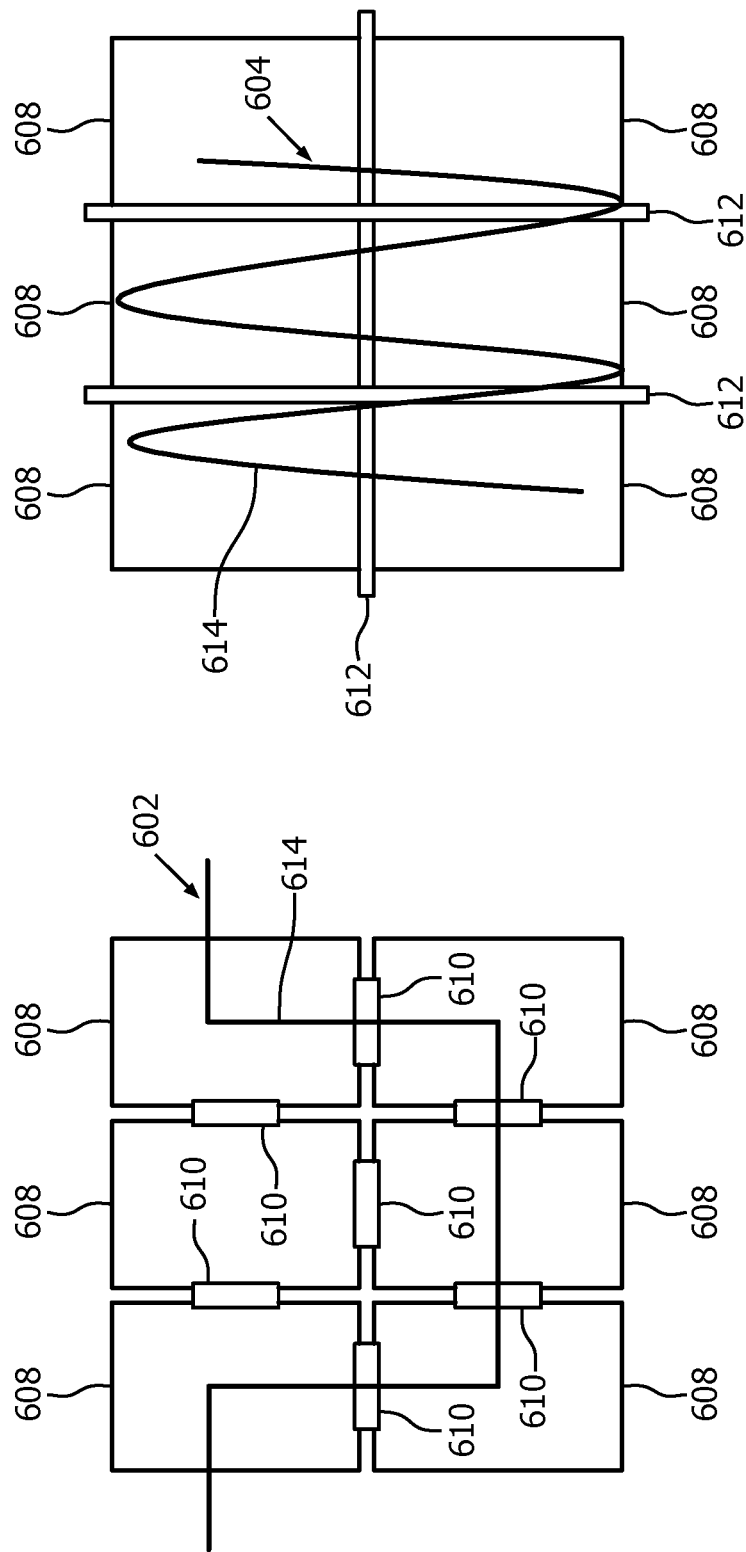
FIG. 6 shows diagrams of alternate shape sensing optical fiber patterns arranged in two dimensional layouts in accordance with another illustrative embodiment.

Referring to FIG. 6, stiffeners 608 may be arranged with other shapes and configurations as well as with different configurations of shape sensing optical fibers 614. FIG. 6 shows two illustrative shape sensing optical fiber patterns 602, 604 relative to stiffeners 608. Other configurations and patterns are also contemplated.

Furthermore, interlocking links 610, 612 may be coupled to all or selected stiffeners 608 (in these and/or other embodiments) to control stiffness over areas of the flexible transducer device. Links 610, 612 may be connected between stiffeners 608 or overlap adjacent stiffeners 608. Links 610, 612 may be clipped into, adhered to or otherwise either permanently or temporarily secured between the stiffeners 608. Links 610, 612 may include a polymeric structure although other materials may be employed. Links 610, 612 may include a plurality of stiffnesses and may be interchangeable to make different sections of the device stiffer than others or to adjust the overall stiffness for different applications, e.g., imaging different areas of the body.

It should be understood that the aspects described herein may be configured in any useful combination. For example, the embodiments described herein may include interlocking links, multiple OSS fibers, different stiffeners arrangements, etc.

Figure 7:
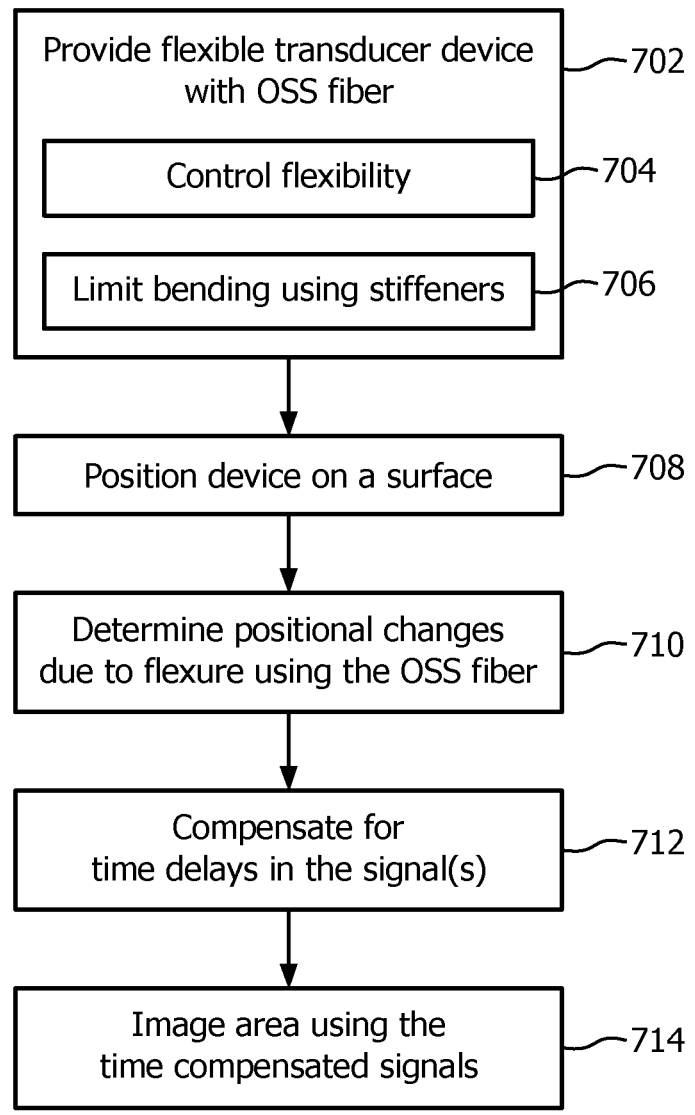
FIG. 7 is a block/flow diagram showing a method for flexible transducing using an optical shape sensing fiber or fibers in accordance with illustrative embodiments.

Referring to FIG. 7, a system/method for flexible transducing is shown and described in accordance with illustrative embodiments. In block 702, a transducer device is provided having a transducer array configured on a substrate. The substrate is configured to flex in accordance with a surface upon which it interacts. The transducer array includes a plurality of elements for transmitting and/or receiving acoustic energy, e.g., ultrasound. At least one shape sensing optical fiber is disposed within the array and configured for shape sensing a position of at least one element in the array. A plurality of stiffeners are connected to the array and configured to flex in accordance with the surface and provide a limit to an amount of flexure. The substrate may include integrated circuits and the elements electrically connected to the integrated circuits.

In block 704, flexibility of the array can be increased (or decreased) by controlling a thickness of at least one of the substrate and the elements. In addition, interlocking links may be employed between or on the stiffeners to control flexibility. In block 706, bending of the array is limited to only one axis, to two axes, etc. by employing the stiffeners and their configuration from block 702. Interlocking links may also be employed to change the flexibility characteristics. These links may be included to form different stiffness patterns or to adjust overall stiffness. Interlocking links are employed to link or join the stiffeners.

In block 708, the transducer device is positioned at the surface for imaging such that the array flexes in accordance with the surface. The surface may be a human body, a mechanical device or any other surface, which may cause flexure of the array when contacted therewith.

In block 710, positional changes in the array on the surface are determined (due to flexure) using the at least one shape sensing optical fiber disposed within the array. In block 712, time delays due to the positional changes in the array are compensated for to improve ultrasonic beam focus. The time delays are delays in the received or transmitted signal due to additional physical distances as a result of flexure of the array. In block 714, areas adjacent to the surface are imaged using the time compensated signals computed using the position information obtained by the at least one shape sensing optical fiber.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for shape sensing for flexible ultrasound transducers (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A transducer device, comprising:
  a transducer array configured on a substrate, the substrate configured to flex in accordance with a surface, the transducer array including a plurality of elements for transmitting and/or receiving acoustic energy;
  at least one shape sensing optical fiber configured to shape sense a position of at least one element in the array;
  a plurality of stiffeners configured to flex in accordance with the surface and provide a limit to an amount of flexure and connected to the substrate such that the substrate is disposed between the plurality of stiffeners and the transducer array; and
  a processor in communication with a memory, the processor configured to receive optical signals from the at least one shape sensing optical fiber and interpret the optical signals to be used in determining time delays based on positions of the elements due to flexure.

2. The device as recited in claim 1, wherein the stiffeners extend longitudinally in one direction and limit bending to only one axis.

3. The device as recited in claim 2, wherein the at least one shape sensing optical fiber extends perpendicularly to longitudinal gaps between the stiffeners.

4. The device as recited in claim 1, wherein the stiffeners extend longitudinally with gaps perpendicular to the longitudinal direction and permit bending in at least two axes.

5. The device as recited in claim 4, wherein the at least one shape sensing optical fiber extends perpendicularly to longitudinal gaps and the gaps perpendicular to the longitudinal direction between the stiffeners.

6. The device as recited in claim 1, wherein the substrate includes integrated circuits and the elements electrically connect to the integrated circuits.

7. The device as recited in claim 1, wherein at least one of the substrate and the stiffeners are configured to adjust flexibility of the array.

8. The system as recited in claim 1, wherein the time delays are compensated for to improve beam focus.

9. A method for flexible transducing, comprising:
providing a transducer device having a transducer array configured on a substrate, the substrate being configured to flex in accordance with a surface, the transducer array including a plurality of elements for transmitting and/or receiving acoustic energy; at least one shape sensing optical fiber configured to shape sense a position of at least one element in the array; and a plurality of stiffeners connected to the substrate such that the substrate is disposed between the plurality of stiffeners and the transducer array and configured to flex in accordance with the surface and provide a limit to an amount of flexure;
positioning the transducer device at the surface for imaging such that the array flexes in accordance with the surface;
determining positional changes in the array on the surface using the at least one shape sensing optical fiber disposed within the array; and
compensating for time delays due to the positional changes to improve ultrasonic beam focus.

10. The method as recited in claim 9, further comprising limiting bending of the array to only one axis by employing the stiffeners.

11. The method as recited in claim 9, further comprising limiting bending of the array to two axes by employing the stiffeners.

12. The method as recited in claim 9, wherein the substrate includes integrated circuits and the elements electrically connect to the integrated circuits.

13. The method as recited in claim 9, further comprising adjusting flexibility of the array by configuring at least one of a thickness of the substrate and connections between the stiffeners.

* * * * *